(12) United States Patent
Shinkai et al.

(10) Patent No.: US 7,745,596 B2
(45) Date of Patent: Jun. 29, 2010

(54) NUCLEAR TRANSPORT NUCLEIC ACID DELIVERY VECTOR

(75) Inventors: Seiji Shinkai, Fukuoka (JP); Takeshi Nagasaki, Nishinomiya (JP); Takeshi Kawazu, Osaka (JP); Shinji Kakimoto, Osaka (JP)

(73) Assignee: Japan Science and Technology Agency, Saitama (JP)

( * ) Notice: Subject to any disclaimer, the term of this patent is extended or adjusted under 35 U.S.C. 154(b) by 267 days.

(21) Appl. No.: 11/632,138

(22) PCT Filed: Jul. 11, 2005

(86) PCT No.: PCT/JP2005/012762

§ 371 (c)(1),
(2), (4) Date: Jul. 2, 2007

(87) PCT Pub. No.: WO2006/006561

PCT Pub. Date: Jan. 19, 2006

(65) Prior Publication Data

US 2007/0281356 A1 Dec. 6, 2007

(30) Foreign Application Priority Data

Jul. 12, 2004 (JP) ............................. 2004-204286
Nov. 17, 2004 (JP) ............................. 2004-332892

(51) Int. Cl.
*C07H 21/02* (2006.01)
*C12N 15/00* (2006.01)

(52) U.S. Cl. .................................. 536/23.1; 435/320.1
(58) Field of Classification Search ................ 536/23.1; 435/320.1

See application file for complete search history.

(56) References Cited

U.S. PATENT DOCUMENTS 5,824,837 A * 10/1998 Chen et al. ...................... 800/3
6,379,966 B2 * 4/2002 Monahan et al. ............ 435/455

OTHER PUBLICATIONS

O'Neill et al. J Biol Chem 270(39):22701-22704, 1995.*
Chan et al. Gene Therapy 7:1690-1697, 2000.*
Yang et al. Radiology 228:36-49, 2003.*
Tomasoni & Benigni. Current Gene Therapy 4:115-122, 2004.*
Gautam et al. Am J Respir Med 1(1):35-46, 2002.*
Nagasaki et al. J Controlled Release 103:199-207, Mar. 2005.*
Bene, A., et al., Nucleic Acid Res., 32, e142 (2004).
Minari, J., et al., Bull Chem Soc. Jpn. 80, 1091-1098 (2007).
Cho, et al., Polycation Gene Delivery Systems: Escape from Endosomes to Cytosol, *Journal of Pharmacy and Pharmacology*, JPP 2003, 55:721-734.
Collas, et al., Nuclear Localization Signals: A Driving Force for Nuclear Transport of Plasmid DNA in Zebrafish, *Biochem. Cell Biol.*, 75:633-640 (1997).
Görlich, et al., Distinct Functions for the Two Importin Subunits in Nuclear Protein Import, *Nature*, vol. 377, 246-248, Sep. 21, 1995.
Hacein-Bey-Abina, et al., LMO2-Associated Clonal T Cell Proliferation in Two Patients after Gene Therapy for SCID-X1, *Science*, 302, 415 (2003).
Huang, et al., Nonviral Vectors for Gene Therapy, *Ernst Wagner*, 1999, back cover only.
Imamoto, et al., The Nuclear Pore-Targeting Complex Binds to Nuclear Pores After Association with a Karyophile, *FEBS Letters*, 368, 415-419 (1995).
Jäkel, et al., Importin β, transportin, RanBP5, and RanBP7 Mediate Nuclear Import of Ribosomal Proteins in Mammalian Cells, *The EMBO Journal*, vol. 17, No. 15, pp. 4491-4502, 1998.
Kaneda, et al., Hemagglutinating Virus of Japan (HVJ) Envelope Vector as a Versatile Gene Delivery System, *Molecular Therapy*, vol. 6, No. 2, Aug. 2002.
Kose, et al., Ran-Unassisted Nuclear Migration of a 97-kD Component of Nuclear Pore-Targeting Complex, *The Journal of Cell Biology*, vol. 139, No. 4, Nov. 17, 1997.
Kutay, et al., Export of Importin α from the Nucleus Is Mediated by a Specific Nuclear Transport Factor, *Cell*, vol. 90, 1061-1071, Sep. 19, 1997.
Marshall, Gene Therapy Death Prompts Review of Adenovirus Vector, *Science*, 286, 5448; ProQuest Central p. 2244, Dec. 17, 1999.
Miyata, et al., Block Catiomer Polyplexes with Regulated Densities of Charge and Disulfide Cross-Linking Directed to Enhance Gene Expression, *J. Am. Chem. Soc.*, 126, 2355-2361 (2004).
Nagasaki, et al., Can Nuclear Localization Signals Enhance Nuclear Localization of Plasmid DNA?, *Bioconjugate Chem.*, 14, 282-286 (2003).
Nagoshi, et al., Nuclear Import of Sterol Regulatory Element-Binding Protein-2, a Basic Helix-Loop-Helix-Leucine Zipper (bHLH-Zip)-Containing Transcription Factor, Occurs through the Direct Interaction of Importin β with HLH-Zip, *Molecular Biology of the Cell*, vol. 10, 2221-2233, Jul. 1999.
Okada, et al., Fusion of Cells by HVJ: Requirement of Concentration of Virus Particles at the Site of Contact of Two Cells for Fusion, *Experimental Cell Research*, 52, 34-42 (1968).
Oupicky, et al., Stimuli-Responsive Gene Delivery Vectors, *Molecular Therapeutics*, 5(4):345-350 (2003).

(Continued)

*Primary Examiner*—Thaian N Ton
*Assistant Examiner*—Marcia S Noble
(74) *Attorney, Agent, or Firm*—Fay Sharpe LLP

(57) ABSTRACT

To provide a new technique by which efficient transfection is ensured in delivering a target gene into a cell, disclosed is a nucleic acid construct for nuclear import, which comprises a ternary complex consisting of a nucleic acid substance containing a gene to be delivered into the nucleus of a cell, an importin protein (for example, importin-β) capable of passing through the nuclear pore and involved in the nuclear transport, and a binding substance (for example, polyethyleneimine) bound to both of the nucleic acid substance and the importin protein. Nucleic acid transport from outside of a cell into the cell nucleus can be particularly promoted by administering the nucleic acid construct bound to a cell membrane receptor binding factor and/or a membrane fusing substance, or administering the nucleic acid construct encapsulated in a non-viral vector (for example, Sendai virus envelope) having cell membrane permeability and membrane fusing properties.

16 Claims, 5 Drawing Sheets

OTHER PUBLICATIONS

Parente, et al., pH-Dependent Fusion of Phosphatidylcholine Small Vesicles, *The Journal of Biological Chemistry*, vol. 263, No. 10, pp. 2724-2730, Apr. 5, 1988.

Pollard, et al., A Novel Receptor-Mediated Nuclear Protein Import Pathway, *Cell*, vol. 86, 985-994, Sep. 20, 1996.

Qian, et al., Targeted Drug Delivery Via the Transferrin Receptor-Mediated Endocytosis Pathway, *Pharmacological Reviews*, 54:561-587, 2002.

Rexach, et al., Protein Import Into Nuclei: Association and Dissociation Reactions Involving Transport Substrate, Transport Factors, and Nucleoporins, *Cell*, vol. 83, 683-692, Dec. 1, 1995.

Rolland, Advanced Gene Delivery, *CRC Press*, 1999, back cover of book only.

Slattum, et al., Efficient in Vitro and in Vivo Expression of Covalently Modified Plasmid DNA, *Molecular Therapy*, vol. 8, No. 2, Aug. 2003.

Tanimoto, et al., No Enhancement of Nuclear Entry by Direct Conjugation of a Nuclear Localization Signal Peptide to Linearized DNA, *Bioconjugate Chem.*, 14, 1197-1202 (2003).

Vyas, et al., Ligand-Receptor-Mediated Drug Delivery: An Emerging Paradigm in Cellular Drug Targeting, *Critical Reviews™ in Therapeutic Drug Carrier Systems*, 18(1):1-76 (2001).

Wiethoff, et al., Barriers to Nonviral Gene Delivery, *Journal of Pharmaceutical Sciences*, vol. 92, No. 2, Feb. 2003.

Yoneda, How Proteins Are Transported from Cytoplasm to the Nucleus, *J. Biochem.*, 121, 811-817 (1997).

Zanta, et al., Gene Delivery: A Single Nuclear Localization Signal Peptide is Sufficient to Carry DNA to the Cell Nucleus, *Proc. Natl. Acad. Sci.*, vol. 96, pp. 91-96, Jan. 1999.

Huang, et al., Nonviral Vectors for Gene Therapy, *Ernst Wagner*, Chapter 1, pp. 3-22 (1999).

Rolland, Advanced Gene Delivery: from concepts to pharmaceutical products, *Harwood Academic, CRC Press*, Chapter 4, pp. 65-102 (1999).

* cited by examiner

[Figure 1]
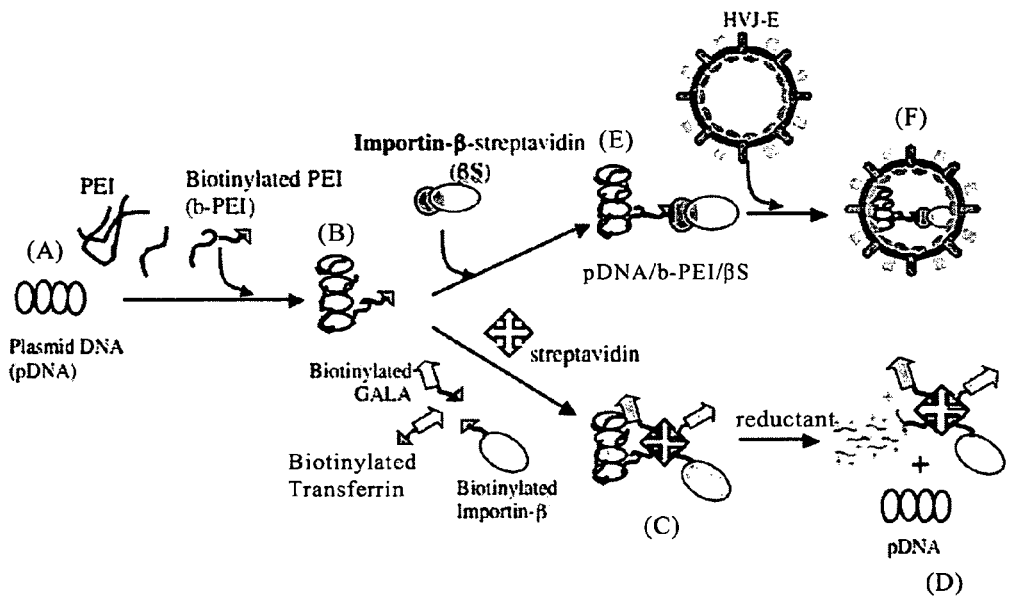
[Figure 2]
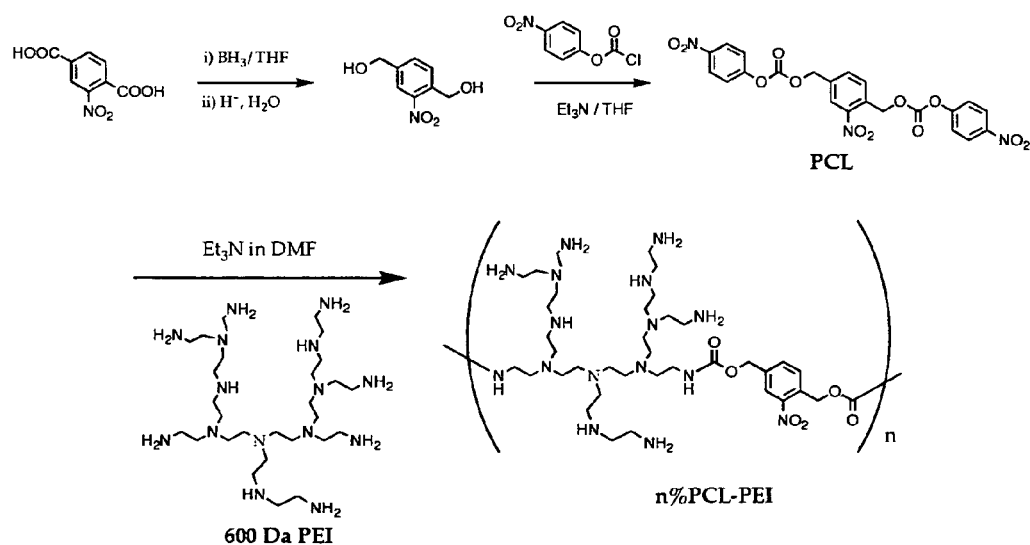

[Figure 3]
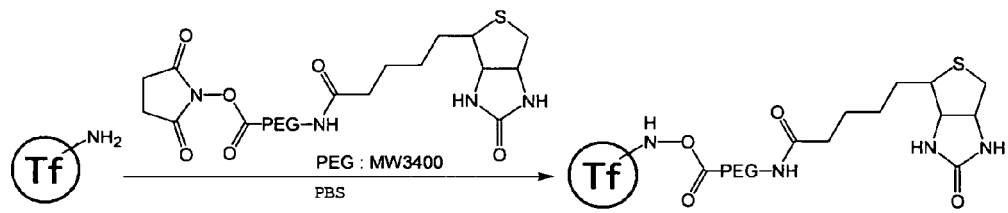
[Figure 4]
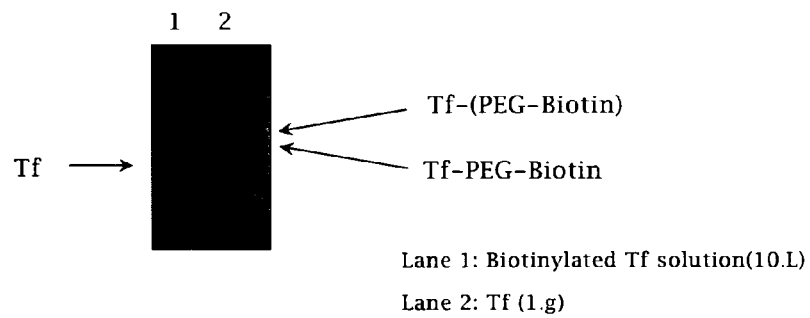
Lane 1: Biotinylated Tf solution(10.L)
Lane 2: Tf (1.g)
[Figure 5]
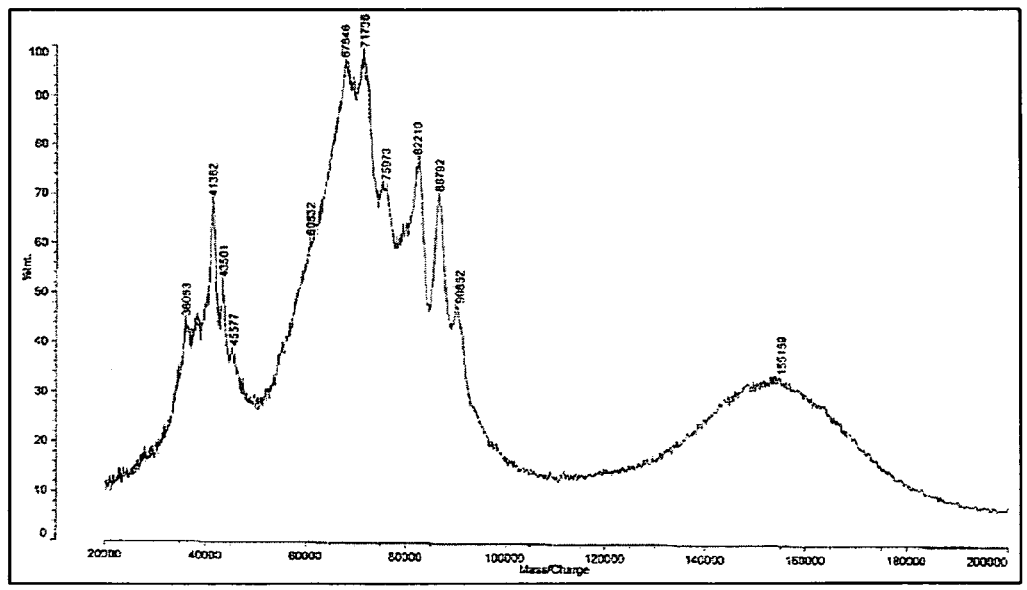

[Figure 6]
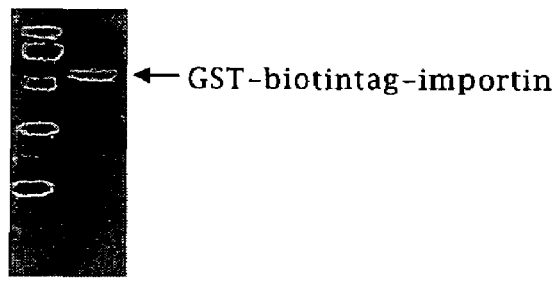
[Figure 7]
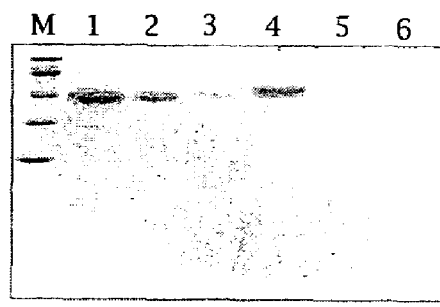
[Figure 8]
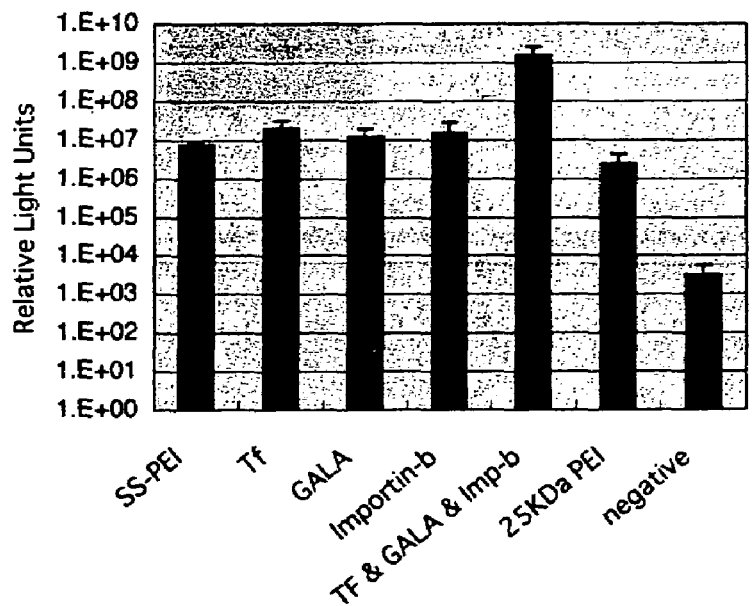

[Figure 9]
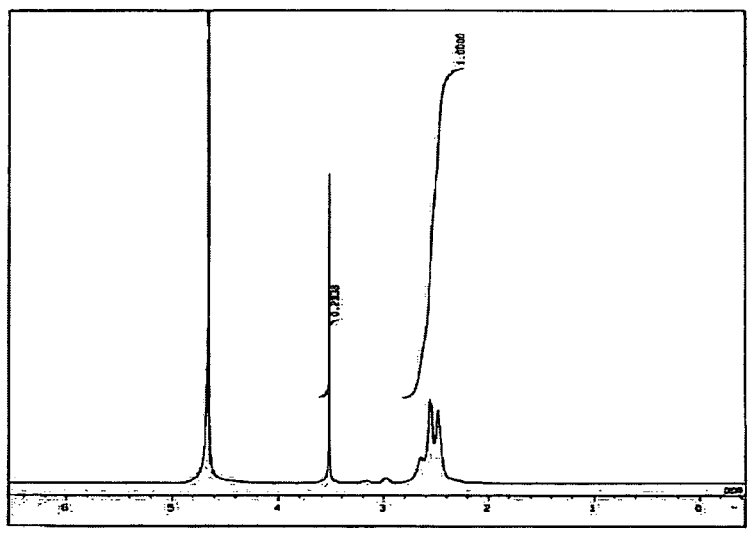
[Figure 10]
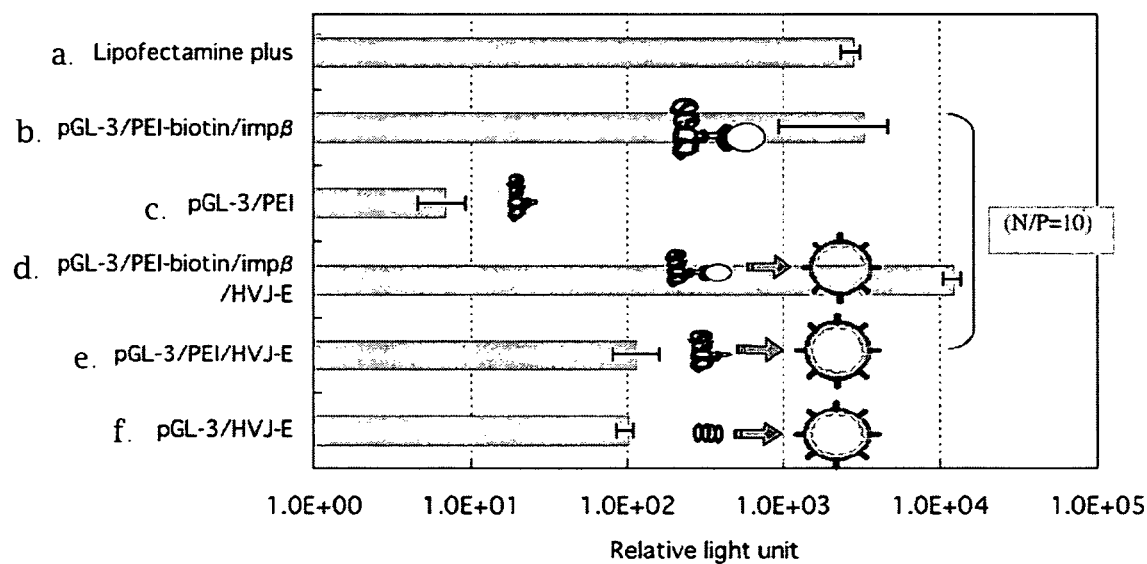

[Figure 11]
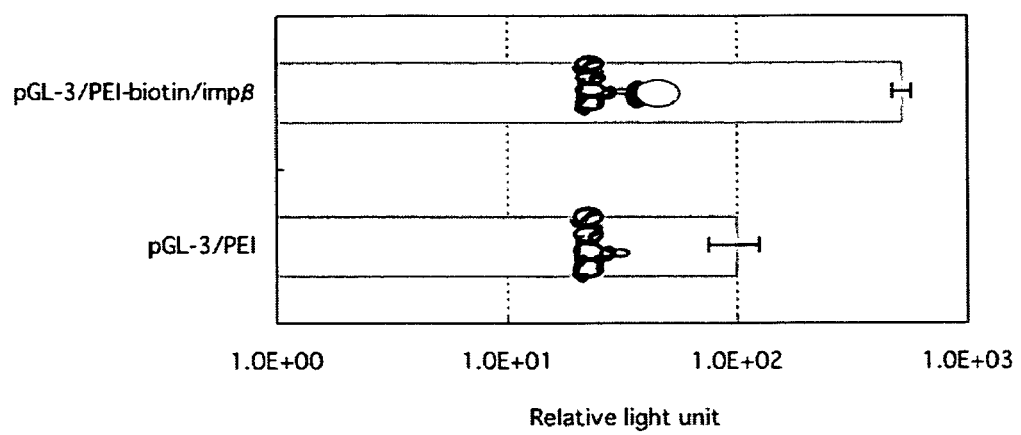

NUCLEAR TRANSPORT NUCLEIC ACID DELIVERY VECTOR

TECHNICAL FIELD

The present invention relates to a novel nucleic acid construct or structure which functions as a non-viral vector with an improved transfection efficiency, and to a method for gene delivery into cells utilizing the same.

BACKGROUND ART

Transfection, a process for delivering an exogenous specific gene into cells, is an indispensable way for obtaining useful information for the treatment of diseases and the development of medicines, by analyzing the action mechanism in which the gene is involved. In such transfection, trials have been recently made to use non-viral effects in order to avoid harmful effects upon the organism. It has been pointed out that there are big barriers to the improvement of transfection efficiency with a non-viral vector, including the passage through the cytomembrane, the escape from transport vesicles, the nuclear import, and the DNA release of a nucleic acid until the nucleic acid is lead to the transcription reaction.

Non-patent reference 1: MarShall, E. (1999) Science 286, 2244-2245.

Non-patent reference 2: Hacein-Bey-Abina, S., Von Kalle, C., Schmidt, M., McCormack, M. P., Wulffrat, N., Leboulch, P., Lim, A., Osborne, C, S., Pawliuk, R., Morillion, E., Sorensen, R., Forster, A., Fraser, P., Cohen, J. I., de Saint Basile, G., Alexander, I., W intergerst, U., Frebourg., T., Aurias, A. D., Stoppa-Lyonnet, D., Romana, S., Radford-Weiss, I., Gross, F., Valensi, F., Delabesse, E., Macintyre, E., Sigaux, F., Soulier, J., Leiva, L. E., Wissler, M., Prinz, C., Rabbitts, J., Le Deist, F., Fischer, A., and Cavazzana-Calvo M. (2003) Science 302, 415-419.

Non-patent reference 3: Huang, L., Hung, M.-C., and Wagner E. (1999) Nonviral Vectors for Gene Therapy, Academic-Press, San Diego.

Non-patent reference 4: Rolland, A (1999) Advanced Gene Delivery, Harwood Academic Publishers, Amsterdam.

Non-patent reference 5: Wiethoff, C. M., and Middaugh, C. R. (2003) J. Pharm. Sci., 92, 203-217.

As a way to improve the cytomembrane passage, utilization of cell membrane receptor-binding factors has been studied, and an improvement is seen via the receptor-mediated endocytosis.

Non-patent reference 6: Vyas S P, Singh A. Sihorkar V. (2001) Crit Rev Ther Drug Carrier Syst., 18(1), 1-76.

Most of non-viral vectors can pass through the cell membrane via endocytosis, but, if they are left as they are, decompose resulting in a low expression efficiency. Thus, as a measure to improve the escape from transport vesicles, studies have been conducted on the utilization of pH-sensitive membrane-fusing substances, with recognized effectiveness.

Non-patent reference 7: Cho, Y. W., Kim, J. D., and Park, K. (2003) J. Pharm Pharmacol., 55 (6), 721-34.

The nuclear import of exogenous genes can be counted as one of the biggest barriers to the improvement of transfection efficiency in the use of non-viral vectors. As an approach for overcoming this issue, extensive studies have been made on the utilization of the nuclear import system of nuclear proteins in eukaryotic cells.

Nuclear proteins are generally tagged with a nuclear localization signal (NLS), to which is bound importin-α, a mediator for the material to be imported. There is finally formed a complex in which importin-β is bound to the importing material, for energy-dependent and selective import of nucleic acid through the nuclear pores present in the nuclear envelope.

Non-patent reference 9: Pexach, M., and Blobel, G., Cell 83, 683-692, (1995).

Non-patent reference 10: Yoneda, Y., J. Biochem, Tokyo 121, 811-817 (1996).

Thus, a number of studies have been made on the promotion of nuclear import and, by extension, the enhancement of expression efficiency, by complexing exogenous gene with a NLS peptide. However, the methodology has not yet been established since advantageous effects are ascertained in some cases, whereas there are some reports negating significant effects on expression efficiency. This may be partly because the formation of the complex proceeds in two-staged reactions resulting in a decreased efficiency.

Non-patent reference 11: Zanta, M. A., Belguise-Valladier, P., and Behr, J. P., Proc. Natl. Acad. Sci. U.S.A. 96 91-96 (1999).

Non-patent reference 12: Collas, P., and Alestrom, P., Biochem. Cell. Biol., 75, 6333-640(1997).

Patent reference 1: Japanese Patent Application Publication No. 1999-506935.

Patent reference 2: Japanese Patent Application Publication No. 2002-514892.

Patent reference 3: Japanese Patent Application Publication No. 2002-533088.

Non-patent reference 13: Nagasaki, T., Myohoji, T., Tachibana, T., and Tamagaki., S., Bioconjugate Chem., 14, 282-286 (2003).

Non-patent reference 14: Tanimoto, M., Kamiya, H., Minakawa, N., Matsuda, A and Harashuma, H., Bioconjugate Chem., 14, 1197-1202 (2003).

It is further to be noted that the expression efficiency is lowered when the exogenous gene is imported into the nucleus as it is bound with the carrier compound which functions as a non-viral vector. Therefore studies have been made on stimuli-responsive carriers, such as photo-responsive or redox-responsive carriers, for the enhancement of DNA release in the nucleus.

Non-patent reference 15: Miyata, K., Kakizawa, Y., Nishiyama, N., Harada, A., Yamazaki, Y., Koyama, H., Kataoka, K (2004) J Am Chem Soc., 126 (8), 2355-61.

Thus, although means have been proposed, on a piecemeal basis, for overcoming the barriers to non-viral vectors in the transport process of a nucleic acid from outside of a cell into the cell nucleus, there are found no organized systems providing collective advantageous effects by the non-viral vectors with a satisfactory efficiency.

PROBLEMS TO BE SOLVED BY THE INVENTION DISCLOSURE OF THE INVENTION

The object of the present invention is to provide a new methodology by which a variety of barriers are overcome in the delivery process of a desired gene extracellularly introduced into cell nucleus, in order to ensure an efficient transfection.

Means for Solving the Problems

The present inventors have succeeded in the preparation of a novel construct or structure comprising a specific intracellular factor involved in the nuclear protein transport and a gene to be delivered, and found that the construct exhibits excellent transfection ability, to achieve the present invention.

Thus, according to the present invention there is provided a nuclear import nucleic acid construct for nuclear import, which comprises a ternary complex consisting of a nucleic acid substance containing a gene to be delivered into the nucleus of a cell, an importin protein capable of passing through a nuclear pore and involved in the nuclear transport, and a binding substance bound to both the nucleic acid substance and the importin protein, as well as a method for gene delivery into a cell comprising the step of contacting the nucleic acid construct with the cell.

BRIEF DESCRIPTION OF THE DRAWINGS

FIG. 1 is a schematic illustration of how the nucleic acid construct of the present invention is prepared and delivered into a cell.

FIG. 2 shows a reaction scheme for synthesizing photoresponsive polyethyleneimine for use in the present invention.

FIG. 3 shows a reaction scheme for synthesizing biotin-labeled transferrin for use in preparing the nucleic acid construct of the present invention (Example 1).

FIG. 4 shows the results of native PAGE of biotin-labeled transferrin for use in preparing the nucleic acid construct of the present invention (Example 2).

FIG. 5 shows the MALDI-TOF Mass spectrum of biotin-labeled transferrin for use in preparing the nucleic acid construct of the present invention (Example 1).

FIG. 6 shows the results of SDS PAGE of GST-biotin tag-importin-β for use in preparing the nucleic acid construct of the present invention (Example 4).

FIG. 7 is for verifying the biotinylation of GST-biotin tag-importin-β for use in preparing the nucleic acid construct of the present invention (Example 5).

FIG. 8 shows the results of in vitro transfection with the nucleic acid construct of the present invention (Example 7). SS-PEI (disulfide-crosslinked-iminothiolane/PEI, 25 KDa polyethyleneimine), Tf (biotinylated transferrin), GALA (biotinylated GALA), Importin-β (biotinylated importin-β), negative (pGL3 plasmid only).

FIG. 9 shows $^1$H-NMR spectrum of the biotinylated polyethyleneimine (Example 8).

FIG. 10 shows expression efficiency data as the results of the transfection experiments conducted with several samples including the nucleic acid construct and its encapsulated body in HVJ-E according to the present invention (Example 9).

FIG. 11 shows expression efficiency data as the results of transfection experiments conducted with the nucleic acid construct using primary fibroblast (Example 10).

BEST MODE FOR CARRYING OUT THE INVENTION

The nucleic acid construct of the present invention is a ternary complex composed of a nucleic acid substance containing a gene to be delivered, an importin protein capable of passing through a nuclear pore and involved in the nuclear transport, and a binding substance mediating between the two.

As the importin protein for the present invention, any can be used as long as it is capable of passing through the nuclear pore and it is involved in the nuclear transport. Specifically, examples include importin-β, importin-7, transportin, transportin-SR, and CAS protein, wherein importin-β is the most preferred.

The amino acid sequences (or base sequences) and functions of the importin proteins can be known, for example, from the following references.

Non-patent reference 16: Jakel, S., and Gorich, D. (1998) EMBO J., 17, 4491.

Non-patent reference 17: Imamoto., N., Shimamoto, T., Kose, S., Takao, z T., Tachibana, T. Matshbae, M., Sekimoto, T., Shimonishi, Y., and Yoneda, Y. (1995), FEBS Lett., 368. 415-419.

Non-patent reference 18: Polland, V. W., Michael, W. M., Nakielny, S., Siomi, M. C., Wang, F., and Dreyfuss, G. (1996) Cell, 86, 985-994.

Non-patent reference 19: Nagoshi, E., Iwamoto, N., Sato, R., and Yoneda, Y., (2999) Mol. Biol. Cell, 10, 2221-2233.

Non-patent reference 20: Kutay, U., Bischoff, F. R., Kostka, S., Kraft, R., and Gorlich, D. (1997) Cell, 90, 1061-71.

As the binding substance for composing the nucleic acid construct of the present invention any substance can be used as long as it is cytocompatible or biocompatible and it is capable of binding to an importin protein or it can be modified so as to be capable of binding to an importin protein. Preferred binding substances are polycationic substances (cationic polymers) typified by polyethylene imine, as described later, polylysine, chitosan and their derivatives. Applicable binding substances are not limited to the above-mentioned, but may include saccharides, proteins, lipids and the like as well.

It is preferred that the binding between the binding substance and the nucleic acid substance containing a desired gene is via a non-covalent bond so that the nucleic acid substance is not influenced (or it is kept intact). For example, in the case where a polycationic substance (cationic polymer) as the binding substance, the nucleic acid substance containing a gene to be delivered into a cell, which is anionic, binds to the cationic polymer through electrostatic interaction.

The binding between the binding substance (preferably a polycationic substance) and an importin protein is via a covalent bond or a non-covalent specific interaction. The covalent bond is exemplified by the use of an ordinary bifunctional reactant, such as a bifunctional dicarboxylate ester, which is rendered to react with the amino group in the importin protein so as to form a conjugate (complex). However, such method suffers from difficulty of synthesis, for example, because the stoichiometry must be controlled.

The non-covalent specific interaction is more preferable than the covalent bond, because a variety of reaction systems conventionally known in the field of biochemistry can be utilized. Specifically, examples include GST (glutathione S-transferase)/glutathione interaction, chitin/chitin-binding protein interaction, histidine tag/nickel complex interaction, biotin/avidin (streptavidin) interaction and the like. For example, a polycationic substance is modified with glutathione, chitin, nickel-complex, or biotin, while an importin protein is bound to GST protein, chitin-binding protein, histidine tag, or avidin, respectively. Thus, conjugates consisting of the polycationic substance and the importin protein can be prepared via the specific interactions of the respective reaction systems.

Of the above-exemplified reaction systems for non-covalent specific interactions, a biotin-avidin system is the most preferably utilized because of the high binding strength. Particularly, streptavidin is capable of forming a tetramer which forms highly stable binding with biotin (the dissociation constant $<10^{15}$).

Thus, in a preferred embodiment of the nucleic acid construct for nuclear import of the present invention, a polycation substance is biotinylated, and the biotinylated polycation substance is bound to an importin protein via the biotin-avidin interaction. More specifically, the biotinylated polycation substance (preferably polyethyleneimine) is rendered to react (i) with biotinylated importin protein in the presence of avidin (preferably streptavidin), or (ii) with a conjugated protein composed of importin protein and avidin (preferably streptavidin).

In a preferred embodiment of the present invention, the polycationic substance, as the binding substance bound to both of the nucleic acid substance and the importin protein, is a cationic polymer which is stimuli-responsive so as to decompose to low molecular substances. The low molecular substances have a lowered affinity with DNA thereby promoting the DNA release. Examples of preferred cationic polymer include polyamines (e.g. polyethyleneimine, polylysine, chitosan, polyamidoamine dendrimer).

Such cationic polymer is imparted with a stimuli-responsive site, more specifically a site which is responsive to an intracellular reductant or light so as to decompose to low molecular substances. A preferred example of the former is the provision of disulfide crosslinkage so that the polymer will decompose to low molecular substances due to the cleavage of the disulfide bonds by glutathione abundantly present in the cells. Thus, a particularly preferred cationic polymer for use in the present invention is polyethyleneimine (PEI) having a disulfide crosslinkage. A photo-responsive cationic polymer can be prepared, for example, by crosslinking polyethyleneimine (PEI) with o-nitrobenzyl structure, a photo-cleavable group, through a photo-cleavable linker (cf. FIG. 2).

Non-patent reference 21: Oupicky, D., Diwadkar, V. (2003) Curr. Opin. Mol. Ther., 5(4), 345-50.

In the context of the present invention, the term "nucleic acid substance" means a gene itself to be delivered into a cell or nucleic acid or the like containing the gene, encompassing any form insofar as it can be bound to the binding substance, typified by the cationic polymers, in the above-mentioned manner. Thus, while the nucleic acid substances include RNA, oligoDNA, single stranded nucleic acid, double stranded nucleic acid, plasmid DNA and the like, the most suitable nucleic acid substance is plasmid DNA from the standpoint of practical use. As use herein, the term "plasmid DNA" generally means an expression vector in which there is encoded, downstream of a promoter, a protein to be expressed, with a base sequence depending upon the target protein.

Thus, according to the present invention, a gene to be delivered is brought into contract with target cells, in the form of a nucleic acid construct composed of a ternary complex in which the gene is in combination with an importin protein (preferably importin-β) via a binding substance (preferably the cationic polymer), thereby effecting nuclear import and further, in a preferred embodiment, the stimuli-responsive cationic polymer decomposes to low molecular substance, promoting the DNA release in the nuclei, for highly efficient gene delivery and expression in the cells.

According to a particularly preferred embodiment of the present invention, the above-mentioned function of the nucleic acid construct can be even more improved, in one of the following two manners, resulting in more efficient and ensured transport of a target gene extracellularly delivered into the cell nucleus for the intracellular expression.

Thus, according to the first particularly preferred embodiment of the present invention, the binding substance typified by the polycationic substance, composing the nucleic acid construct, is bound not only to an importin protein (capable of passing through the nuclear pore and involved in the nuclear transport) but also to at least one of a cell membrane receptor binding factor and a membrane fusing substance.

As the cell membrane receptor binding factor for the present invention, any substance can be used insofar as it is capable of binding to a cell membrane receptor and migrating into cells via endocytosis. Specific examples thereof include transferrin, EGF (epidermal growth factor), FGF (fibroblast growth factor), HGF (hepatocyte growth factor), NGF (nerve growth factor), TGF (transforming growth factor), LDL (low density lipoprotein), insulin, folic acid, diphtheria toxin, integrin binding factor, asialoglycoprotein receptor binding factor and the like, of which transferrin is the most preferred example.

Non-patent reference 22: Qian, Z. M., Li, H., Sun, H., and Ho, K (2002) Pharmacol Rev., 54(4), 561-87.

As the membrane fusing substance for the present invention, any substance can be used insofar as it is capable of binding to the nucleic acid substance containing a gene to be delivered into the cell nucleus to form a conjugate and fusing with a cell membrane with decreasing pH. Specific examples include influenza virus hemagglutinin HA-2, human immunodeficiency virus Tat, diphtheria toxin T-domain, GALA and the like, of which GALA is the most preferred example.

Non-patent reference 23: Parente, R. A., Nir, S., and Szoka, F. C. Jr. (1988) J Biol Chem., 263(10), 4724-30.

The binding of the binding substance (preferably the polycationic substance) with the cell membrane receptor binding factor and/or the membrane fusing substance can be effected in a similar manner as in the binding between the binding substance and the importin protein. Thus, for example, the biotinylated polycationic substance is rendered to react with biotinylated cell membrane receptor binding factor and/or biotinylated membrane fusing substance.

As explained in the foregoing, streptavidin will form a tetramer which is capable of forming highly stable bond(s) with biotin. Therefore, a complex can be prepared in which four different kinds of substances (for example, a polycationic substance, an importin protein, a cell membrane receptor binding factor, and a membrane fusing substance) are biotinylated to form the complex via streptavidin.

The second particularly preferred embodiment, by which the function of the nucleic acid construct is improved in order to effect efficient and ensured transport of a target gene extracellularly delivered into the cell nucleus for the intracellular expression, is to encapsulate or include the nuclear acid construct in an envelope or capsid of viral origin, for use.

For example, there can be used Sendai virus envelope (HVJ-E), which is known as a substance capable of delivering foreign genes into cells abundantly and efficiently. Sendai virus (Hemagglutinating Virus of Japan: HVJ) is a kind of mouse pneumovirus (no infectiosity to humans) which was discovered in Japan in 1950's. The virus envelope has two types of glycoproteins (F and m), which exhibit strong function in fusing two different types of cells together. HVJ-E vector is directed to the utilization of only the envelope of HVJ which has been cleared of all the genome. As the vector has two types protein on the envelope exhibiting cell fusion function, it is capable of transporting a variety of substances into animal cells in a rapid and efficient manner. In addition, since the virus has been cleared of all the genome, the safety to humans has been established and a large amount of substances can be encapsulated therein. Therefore, it can be an effective tool for use in gene function analysis, gene therapy and drug delivery system.

Non-patent reference 24: Okada, Y. and Murayama, F. Exp Cell Res., 52, 34-42 (1968).

Non-patent reference 25: Kaneda, Y., Nakajima. T., Nishikawa, T., Yamamoto, S., Ikegami, H., Suzuki, N., Nakamra, H., Morishita, R and Kotani, H Mol. Ther., 6, 219-226 (2002).

Patent Reference 4: Japanese Patent Application Publication No. 2001-286282

The envelope or capsid of viral origin for use with the nucleic acid construct of the present invention is not limited to Sendai virus envelope and any one can be used as long as it is capable of transporting a nucleic acid substance into the cytoplasm and it has been cleared of infectiosity to humans. For example, the capsid of hepatitis B virus can be used.

Non-patent reference 26: Slattum, P. S., Loomis, A. G., Machnik, K. J., Watt, M. A., Duzeski J. L., Budker, V. G., Wolff, J. A., and Gorlich, D., Mol. Ther. 8, 255 (2003).

The gene delivery in accordance with the present invention using the above-mentioned envelope or capsid of viral origin can be carried out as follows: The nucleic acid construct composed of a ternary complex of the present invention is admixed and stirred with the envelope or capsid in an appropriate buffer to prepare an transfection solution containing the nuclear acid construct encapsulated in the envelope or capsid. Then, the solution is rendered to contact with cells which have undergone a cytomembrane perforation treatment which is, for example, a surfactant treatment in the case where Sendai virus envelope is used, or an electroporation in the case where hepatitis B virus capsid is used.

FIG. 1 schematically illustrates how the nucleic acid construct of the present invention is prepared and delivered into a cell, in accordance with a preferred embodiment of the present invention as described later in Examples.

In FIG. 1 a plasmid DNA (pDNA) is used as an example of the nucleic acid substance [FIG. 1 (A)]. The pDNA is admixed with biotinylated polyethyleneimine having a disulfide crosslinkage (b-PEI), as the binding substance, followed by an incubation, to prepare a complex (polyionic complex) in which the pDNA is electrostatically bound to b-PEI [FIG. 1 (B)]. This procedure will cause no lowering in the transcription efficiency because no chemical modification (biotinylation) is made on the nucleic acid substance itself. Furthermore, the neucleic acid substance (a polyanion) and the polycation will form a very stable polyionic complex, and the formation of the complex will cause, depending upon the condition, condensation of the nucleic acid substance, thereby facilitating the intracellular transport, particularly the nuclear import.

Next in accordance with the particularly preferred embodiment of the present invention, the importin protein, the cell membrane receptor binding factor, and/or the cell fusion substance are each biotinylated (biotin-labeled) by chemical modification or genetic engineering. The biotinylated ones are bound to one another through streptavidin, to form the nucleic acid construct in which the gene to be delivered is bound, by the cationic polymer, to the importin protein and also to the cell membrane binding receptor factor and/or the cell fusing substance. In the nucleic acid construct as shown in FIG. 1, importin-β is used as the importin protein, transferrin as the cell membrane receptor binding factor, and GALA as the cell fusing substance, each of which is biotinylated and then bound to the p-DNA/b-PEI complex through streptavidin to form the nucleic acid construct [FIG. 1 (C)].

As the thus formed nucleic acid construct is contacted with target cells, it passes through the cell membranes effectively, escapes into the vesicles efficiently into the cytoplasm, and moves into the nuclei without fail. What is more, the DNA release is promoted in the nuclei as the cationic polymer decomposes to low molecular substances due to the intracellular reductant (particularly glutathione) or, if necessary, external light. Thus, intracellular gene delivery and expression can be effected in a very efficient manner. FIG. 1 schematically illustrates an example where disulfide crosslinked, biotinylated polyethyleneimine (b-PEI) decomposes due to the intracellular reductant to release the nucleic acid substance containing the gene (pDNA) [FIG. 1 (D)] (cf. Example 7).

According to the other particularly preferred embodiment of the present invention, the nuclear acid construct is encapsulated in the envelope or capsid of viral origin, followed by contact with cells. Thus, in the example as shown in FIG. 1, the complex [FIG. 1 (B)] of plasmid DNA and biotinylated PEI (the disulfide crosslinkage is not necessarily required in this embodiment) is bound to the importin-β/streptavidin conjugate protein [FIG. 1 (E)], and the resultant is encapsulated in Sendai virus envelope (HVJ-E), followed by the contact with cells. This embodiment also ensures the nuclear import of the nuclear acid construct for efficient gene expression (cf. Example 9).

The present invention is utilized in the delivery of a specific gene into cells, the cloning of the gene and the expression of a protein encoded by the gene, in which the target genes are not restricted and the principle of the present invention can be applied to any type of eukaryotic cells, particularly to animal cells. It is however preferred that the origin of cells membrane receptor binding factor or importin protein employed is the same in species as that of the target cell.

In order to explain more specifically the characteristic features of the present invention, there are set out in the following working examples, which relate to: the preparation of biotinylated, disulfide crosslinked polyethyleneimine, biotinylated, disulfide crosslinked polyethyleneimine, biotinylated transferrin, biotinylated GALA, and biotinylated importin-β, for composing a nucleic acid construct of the present invention, the encapsulation of the nucleic acid construct in Sendai virus envelope, and in vitro experiments for protein expression using the same. However, the present invention is not restricted by these examples.

EXAMPLE 1

Preparation of Biotin-labeled Transferrin (Tf)

In accordance with the synthesis scheme as illustrated in FIG. 3, a solution of Biotin-PEG-NHS [ω-biotincarboxylate-N-hydroxysuccinate-imide ester having a PEG (polyethylene glycol) spacer, Searwater] 2.56 mg (0.67 μmol) in 50 μL DMF was added stepwise to a solution of Apo-Transferrin 50 mg (0.67 μmol) dissolved in 1 mL solution of 50 mM PBS solution (pH 7.0) at 4□ under shaking, and the resultant was further shaken for fifteen hours at 4□. The resultant solution was subjected to a centrifugation (3000×g) at 4□ with a molecular sieve filter (MW 10000), to remove impurities until it was concentrated to a volume of 900 μL. The purification of the biotinylated Tf was carried out with Soflink™ Soft Release Avidin Resin (Promega). Thus, Softlink™ Soft Release Avidin Resin 500 μL was suspended in a 5 mL solution of 50 mM PBS, followed by a centrifugation for five minutes at 4□, 1000×g.

After remoral of the supernatant, the resultant was suspended in a 500 mL solution of 50 mM PBS, and added to the above-mentioned reaction solution, followed by a gentle stirring at 4□ overnight. Then, the supernatant was removed, followed by washing with 50 mM PBS three times to remove Tf left unreacted. A 5 ml solution of 5 mM biotin was added, followed by a gentle stirring at 4□ overnight. A centrifugation was conducted at 4□, 1000×g, for five minutes, and the supernatant was subjected to a centrifugation with a molecular sieve filter (MW 10000) at 4□, 3000×g, to remove isolated biotin. The resultant solution was subjected to a gel filtration with a PD-10 column which had been equilibrated with 50 mM PBS in advance. Fractionation was conducted by every 1 mL to determine a fraction containing the biotinylated Tf by means of UV measurement. The fraction solution was concentrated with a molecular sieve filter (MW 3000). The rate of introduction of biotin was determined by native PAGE (FIG. 4) and MALDI-TOFMS (FIG. 5) with the result that the rate of introduction of Biotin-PEG was calculated to be 1.5 per one molecule of transferrin.

EXAMPLE 2

Synthesis of Biotin-PEG Bonded GALA

By Fmoc solid phase synthesis was prepared a peptide composed of pH-responsive peptide GALA (thirty aminoacid residues: WEAALAEALAEALAEHLAEALAE-ALEALA4) with the N-terminus thereof being bonded with Biotin-PEG. Isolation was conducted by high performance liquid chromatography.

EXAMPLE 3

Construction of Expression Vector
(p-GEX-2T-biotin-importin-β)

Peptide sequence (biotin tag), which is to be bonded to a protein expression vector Pinpoint Xa-3 (Promega), was amplified by PCR using the following primers. The primers are so designed that the biotin tag has a BamHI site at each terminus.

```
5'-GCCCGCGGATCCATGAAACTGAAGGTAACA-3'

5'-GATATCGGTACCGGATCCCAGCTGAAGCTT-'3
```

The amplified biotin tag was purified by phenol-chloroform extraction and ethanol precipitation. The purified biotin tag and a protein expression vector pGEX-2T-importin-β (prepared in the manner described in non-patent reference 27) encoding a gene for GST-importin-β fusion protein were each treated with BamHI, followed by phenol-chloroform extraction and ethanol precipitation for purification. The BamHI-treated biotin tag and pGEX-2T-importin-β were admixed with each other at a molar ratio of 10:1, to insert the biotin tag into the BamHI sites of pGEX-2T-importin-β using Ligation High (Toyobo). The solution after the ligation was transformed into competent cells of E. coli JMI09 (Nippon Gene), and the target pGET-2T-biotin-importin-β was purified from the colonies grown on LB agar medium (containing 100 μg/ml of ampicillin). The expression vector encodes GST-biotin tag-importin-β gene from the 5' terminus (SEQ ID No.1).

Non-patent reference 27: Kose, S., Imamoto, N., Tachibana, T., Shimamoto, T, Yoneda, Y. (1997) J. Cell. Biol., 139, 841-849.

EXAMPLE 4

Expression and Purification of GST-biotin
Tag-importin-β Fusion Protein

The thus constructed expression vector pGEX-2T-biotin tag-importin-β for GST-biotin tag-importin-β fusion protein was transformed into competent cells of E. coli BL21 strain for protein expression (Novergen) to obtain colonies on a LB agar medium (containing 100 μg/ml of ampicillin and 2 μM biotin). The colonies were cultured in a liquid LB agar medium at 37□, and added with isopropylthiogalactoside (IPTG) at a final concentration of 0.5 mM to induce the protein expression at 20□. The cultured E. coli was recovered by centrifugation and washed with 0.9% NaCl solution. The E. coli was again subjected to centrifugation, for recovery, suspended in lysis buffer and frozen with liquid nitrogen. Following fusing on water bath, the resultant was frozen with liquid nitrogen. Fusing on water bath was followed by supersonic treatment and centrifugation to isolate the supernatant.

The supernatant was added with Sepharose 4B (Amersham) to make only the target biotinylated protein adsorb thereon. Glutathione Sepharose 4B was washed with lysis buffer, and then the target protein was eluted with glutathione. After the protein solution was concentrated by ultrafiltration, the protein was purified by replacing the buffer with PBS using PD-10 column (Amersham). The purified protein was divided into fractions which were frozen with liquid nitrogen for strage at −80□. The purification was ascertained by SDS-PAGE analysis (FIG. 6). It is seen that the target substance was purified and isolated as a fusion protein with a molecular weight of 137 kDa composed of GST (26 kDa), biotin tag (14 kDa) and importin-β (97 kDa) as represented by the single bands corresponding to the respective molecular weights.

EXAMPLE 5

Confirmation of Biotinylation of GST-biotin
Tag-importin-β Fusion Protein

GST-biotin tag-importin-β(3 μg) and Avidin Resin (3 μl) (Promega) were mixed together in PBS (15 μl) and gently stirred at 4□ for two hours. Following mild centrifugation to remove the supernatant, there was added 0.5M NaI (15 μl), and the resultant solution was gently stirred at 4□ for fifteen minutes to dissociate the GST-biotin tag-importin-β nonspecifically bound to Avidin Resin. Following mild centrifugation to remove the supernatant, the resultant was washed with PBS to obtain Avidin Resin with GST-biotin tag-importin-β adsorbed thereto. The adsorption of GST-biotin tag-importin-β to Avidin Resin was ascertained by SDS-PAGE analysis (FIG. 7).

The adsorption of the fusion protein on Avidin Resin is clearly higher that of he nonspecific adsorption of the unmodified importin-β on Avidin Resin, evidencing that the importin-β fusion protein was biotinylated. In the electrophoresis diagram, M represents molecular weight markers, 1 represents GST-importin-β before adsorption, 2 represents GST-importin-β supernatant, 3 represents GST-importin-β after adsorption, 4 represents GST-biotin tag-importin-β before adsorption, 5 represents GST-biotin tag-importin-β supernatant, and 6 represents GST-biotin tag-importin-β after adsorption, respectively.

EXAMPLE 6

Synthesis of Biotin-labeled, Disulfide Crosslinked
Polyethyleneimine

Low molecular weight polyethyleneimine (average molecular weight 1800, Wako Pure Chemical) 0.5 g (0.27 mol) was dissolved in 5 mL of DMF. The resultant solution was added with iminothiolane (Aldrich) 100 mg (0.75 mmol), followed by stirring at room temperature in a stream of nitrogen for fifteen hours. The thus obtained reaction solution was concentrated with ultrafiltration filter Centriprep (MW3000) Amicon, followed by washing with 15 ml of ultrapure water. The resultant was then added with 100 mM DTT solution (0.5 mL) and biotin-PEG-TSPA (100 mg) followed by stirring in a stream of nitrogen at room temperature for fifteen hours, The reaction solution was concentrated with ultrafiltration filter Centriprep (MW3000) (Amicon), followed by washing with 5 mM DTT aqueous solution (15 mL). The residue was dissolved in 5 mM DTT solution (5 mL) to obtain a stock solution of biotin-labeled disulfide crosslinked polyethylene imine.

Ultrapure water 2 mL was added to 0.25 mL of the stock solution, followed by air bubbling for two hours. Gel filtration was carried out with Sephadex G-25 in which ultrapure water was used for elution, thereby isolating the low molecular fraction, followed by lyophilization to yield while crystal 30 mg. The rates of introduction of iminothiolane and biotin-PEG were calculated by $^1$H-NMR analysis, the result being twenty molecules of iminothiolane and one molecule of biotin-PEG per ten molecules of the low molecular weight polyethyleneimine. Elemental analysis showed C:50.71, H:10.81, N:24.62%, supporting the results of the NMR analysis. It was also calculated based on the results of elemental analysis that the concentration of nitrogen capable of protonation in the stock solution of biotin-labeled, disulfide crosslinked polyethyleneimine was 2 ml/L.

EXAMPLE 7

In vitro Transfection

In each well of a 24-well plate was placed 1 ml of suspension of A549 cells (human alveolus epithelial cells) (50000 cells/ml) to incubate for 24 hours at 37□ in the presence of $CO_2$. The culture media were removed, followed by addition of 1.25× serum-free DMEM 200 µl per well, and then the transfection isolation 50 µL per well to incubate at 37□ for three hours in the presence of $CO_2$ for contact with the cells. Then the culture media were removed and DMEM was added at 1 mL per well to incubate at 37□ for twenty four hours in the present of $CO_2$, followed by luciferase assay. It is noted that the transfection solution was prepared as follows: To ultrapure water was added 1 µg of pGL3-Control plasmid (a plasmid DNA encoding transferase gene, Promega) and then the stock solution of biotin-labeled, disulfide crosslinked polyethyleneimine (N/P=10), to incubate for ten minutes. Then, there were added biotinylated transferrin, biotinylated GALA, and biotinylated importin-β, singly or in a mixed solution, and finally a solution of streptavidin and incubation was carried out for twenty minutes to prepare a virus-mimicking artificial nuclear acid construct.

The results of the transfection are given in FIG. 8. It is seen that the introduction of the nucleic acid transport-promoting proteins according to the present invention resulted in improvements in transfection efficiency, as compared with 25 kDa PEI. In particular, the use of biotinylated, disulfide crosslinked polyethyleneimine to which all of biotinylated transferrin, biotinylated GALA and biotinylated importin-β were conjugated via streptavidin produced a 600-fold improvement in transfection efficiency, demonstrating great contribution to effective passage through the cell membrane, efficient escape from the transport vesicles into the cytoplasm, ensured nuclear import and intranuclear DNA release of the construct.

EXAMPLE 8

Preparation of Biotinylated Polyethyleneimine

As the binding substance to the plasmid DNA was employed branched polyethyleneimine (PEI, MW25000, Aldrich) which is widely used as a non-viral vector. The biotin-labeling agent employed was Biotin-PEG-$CO_2$—NHS (Nektor) which is composed of a polyethylene glycol chain (MW 3400) having a biotin group and a carboxylate-N-hydroxysuccinimide ester group bonded thereto at the ends. PEI (25 mg) and Biotin-PEG-$CO_2$—NHS (5 mg) are dissolved in DMSO (1050 µL) and the mixture was shaken for twenty four hours at room temperature. The resultant was placed on a molecular sieve filter, Centricon (MW 10000, Amicon), added with distilled water (5 mL) and subjected to centrifugation to remove low molecular components and the solvent (DMSO). Then, lyophilization was carried out to obtain biotinylated PEI as white powder (14.3 mg).

Determination of the Rate of Introduction of Biotin

Elemental analysis of the synthesized biotinylated PEI was conducted, with the result C:49.23%, H:11.02% and N:22.05%. The observed values aren in good agreement with calculated values of C:49.20%, H:11.03% and N:22.10% based on the formula of PEI-(PEG-Biotin)$_{2.2}$ 230H$_2$O. Thus, the number of biotin labels was determined to be 2.2. The number of biotin labels was also checked by the ratio of protons derived from polyethyleneimine (2.3-2.7 ppm) and polyethylene glycol (3.5-3.6 ppm) as shown in $^1$H-NMR spectrum (D$_2$O) of FIG. 9.

EXAMPLE 9

Preparation of Plasmid DNA/biotinylated PEI/importin-β Ternary Complex, Encapsulation in HVJ-E and Transfection In a solution of PBS, 5 µL solution of 0.2 µg/µL PGL3-control vector containing a gene encoding luciferase (pGL-3, Promega) was added with an aqueous solution of 0.77 mM (0.5 µg/µL) biotinylated PEI (biotin-PEI) (1.25 µL) or an aqueous solution of 7.7 mM PEI (3.88 µL), and the mixture was allowed to stand for fifteen minutes at room temperature. Herein, the value of N/P (the ratio of the number of nitrogen atoms in the cationic polymer to the number of phosphate residue group in the DNA) was 10. There was added 0.74 µL solution of 0.05 µg/µL GFP-importin-β-streptavidin fusion protein to prepare the pGL-3/biotin PEI/importin-β-streptavidin ternary complex, wherein the amount of addition corresponds to one equivalent of the biotinylated PEI.

On the other hand, in accordance with the protocol attached to HVJ-E vector kit (Ishihara Sangyo), HVJ-E was thawed and 10 µL thereof was placed in a microtest tube. There was added 2.5 µL of Reagent A, and the mixture was stirred and allowed to stand on ice for five minutes. Following the addition of the above-mentioned ternary complex solution, the mixture was stirred and added with Reagent B (1.5 µL) for stirring. Centrifugation was carried out at 4□, 10000×g, for five minutes to remove the supernatant. Then, the resultant was suspended in the kit buffer (7.5 µL) using a pipette to encapsulate the pGL-3/biotin-PEI/importin-β-streptavidin ternary complex in HVJ-E. After the encapsulation, the resultant was admixed with Reagent C (1.25 µL).

One night prior to transfection experiment, NIH3T3 cells (mouse fetus fibroblast cells) were plated at 50000 cells per well of a 24-well plate. The transfection experiment was carried out by adding the solution of pGL-3/biotin-PEI/importin-β-streptavidin ternary complex encapsulated in HVJ-E to the cells and incubating at 37☐ for twenty four hours in the presence of 5% $CO_2$. For comparison, the gene transfer and expression experiment was also conducted under the protocol with Lipofectamine plus (Invitrogen), one of the most active gene-transferring agents now commercially available. After the incubation, the cells were washed with PBS and relative light intensity was measured with Steady-Glo Luciferase Assay System (Promega) to evaluate the degree of luciferase expression.

The results are shown in FIG. 10. Firstly, in the cases where no encapsulation in HVJ-E was effected in gene delivery into cells, the expression efficiency was very low with PEI/DNA complex (FIG. 10, c), whereas the addition of the nuclear import protein resulted in about 470-fold improvement in expression efficiency (FIG. 10, b), which is comparable or even superior to the use of commercially available Lipofectamine plus (FIG. 10, a). Next, in the case of pGL-3/biotin-PEI/importin-β-streptavidin ternary complex encapsulated in HVJ-E (FIG. 10, d), the expression activity was about 122-fold, compared with the case where only pGL-3 was encapsulated (FIG. 10 f) under the protocol. It is also noted that the encapsulation resulted in about four times in expression efficiency as high as the case of no encapsulation in HVJ-E (FIG. 10, b), demonstrating that, when the nucleic acid for nuclear import construct was effectively delivered into the cytoplasm, importin-β greatly contributed to the subsequent passage through nuclear pore and intranuclear transport of the nucleic acid.

EXAMPLE 10

Transfection into Neonatal Mouse Primary Fibroblast Cells

In a solution of PBS, 5 μL solution of 0.2 μg/μL PGL3-control-vector containing a gene encoding luciferase (pGL-3, Promega) was added with an aqueous solution of 0.77 mM (0.5 μg/μL) biotinylated PEI (biotin-PEI) (1.25 μL) or an aqueous solution of 7.7 mM PEI (3.88 μL), and the mixture was allowed to stand for fifteen minutes at room temperature. Herein, the value of N/P (the ratio of the number of nitrogen atoms in the cationic polymer to the number of phosphate residue group in the DNA) was 10. There was added 0.74 μL solution of 0.05 μg/μL GFP-importin-β-streptavidin fusion protein to prepare the pGL-3/biotin PEI/importin-β-streptavidin ternary complex, wherein the amount of addition corresponded to one equivalent of the biotinylated PEI.

One night prior to transfection experiment, fibroblast cells of neonatal mouse epithelium origin were plated at 50000 cells of a 24-well plate. The transfection experiment was carried out by adding the above-mentioned pGL-3/biotin-PEI/importin-β-streptavidin ternary complex and incubating at 37☐ for twenty four hours in the presence of 5% $CO_2$. For comparison, the gene transfer and expression experiment was also conducted with the substance having no protein for nuclear import. After the incubation, the cells were washed with PBS, and luciferase expression was evaluated with Steady-Glo Luciferase Assay System (Promega).

The results are shown in FIG. 11. Compared with PEI/DNA complex, the addition of the protein for nuclear import resulted in about five-fold improvement in the expression efficiency, suggesting advantageous effects by importin-β even for primary cells.

INDUSTRIAL UTILIZABILITY

The present invention is expected to be utilized in a variety of fields including gene therapy, as a new non-viral technique for delivering a target gene into cells and expressing the same in a highly efficient manner.

The invention claimed is:

1. A nucleic acid complex for nuclear import comprising a nucleic acid encoding a gene to be delivered into the nucleus of a cell, an importin protein capable of passing through a nuclear pore and involved in nuclear transport, and a polycationic binding substance bound to both said nucleic acid and said importin protein, wherein said nucleic acid is bound to said polycationic binding substance via a non-covalent bond such that the gene remains intact, and wherein the binding between said binding substance and said importin protein is via a biotin-avidin interaction in which the polycationic binding substance is biotinylated and bound to the importin protein via a biotin-avidin interaction.

2. The nucleic acid complex for nuclear import as claimed in claim 1, wherein the polycationic binding substance is polyethyleneimine.

3. The nucleic acid complex for nuclear import as claimed in claim 1, wherein the polycationic binding substance is a cationic polymer which is responsive to an intracellular reductant or light so as to decompose into lower molecular weight substances.

4. The nucleic acid complex for nuclear import as claimed in claim 3, wherein the polycationic binding substance is polyethyleneimine having a disulfide crosslinkage.

5. The nucleic acid complex for nuclear import as claimed in claim 1, wherein the importin protein is a protein selected from importin-β, importin 7, transportin, transportin SR, and CAS protein.

6. The nucleic acid complex for nuclear import as claimed in claim 5, wherein the importin protein is importin-β.

7. The nucleic acid complex for nuclear import as claimed in claim 1, wherein the nucleic acid is a plasmid DNA.

8. A nucleic acid complex for nuclear import consisting of:
a) nucleic acid encoding a gene to be delivered into the nucleus of a cell,
b) an importin protein capable of passing through a nuclear pore and involved in nuclear transport,
c) at least one of:
  i) a cell membrane receptor binding factor, and
  ii) a membrane fusing substance, and
d) a polycationic binding substance bound to said nucleic acid, said importin protein, and said at least one of the cell membrane binding factor and the membrane fusing substance, wherein said nucleic acid is bound to said polycationic binding substance via a non-covalent bond such that the gene remains intact, and wherein the binding of the polycationic substance with each of said importin protein and said at least one of the cell membrane receptor binding factor and the membrane fusing substance is via a covalent bond or non-covalent interaction.

9. The nucleic acid complex for nuclear import as claimed in claim 8, wherein the cell membrane receptor binding factor is present in said complex and is selected from transferrin, EGF (epidermal growth factor), FGF (fibroblast growth factor), HGF (hepatocyte growth factor), NGF (nerve growth factor), TGF (transforming growth factor), LDL (low density lipoprotein), insulin, folic acid, diphtheria toxin, integrin binding factor, and asialoglycoprotein receptor binding factor.

10. The nucleic acid complex for nuclear import as claimed in claim 8, wherein the membrane fusing substance is present in said complex and is selected from influenza virus hemagglutinin HA-2, human immunodeficiency virus Tat, GALA, and diphtheria toxin T-domain.

11. The nucleic acid complex for nuclear import as claimed in claim 9, wherein the cell membrane receptor binding factor is transferrin.

12. The nucleic acid complex for nuclear import as claimed in claim 10, wherein the membrane fusing substance is GALA.

13. A nucleic acid complex for nuclear import comprising a) a nucleic acid encoding a gene to be delivered into the nucleus of a cell, b) an importin protein capable of passing through a nuclear pore and involved in nuclear transport, c) optionally, at least one of a cell membrane receptor binding factor and a membrane fusing substance, and d) a binding substance bound to said nucleic acid, said importin protein, and said at least one of the cell membrane receptor binding factor and the membrane fusing substance, where present, said nucleic acid being bound to said binding substance via a non-covalent bond such that the gene remains intact, the binding of said binding substance with said importin protein being via a covalent bond or non-covalent interaction, the binding of said binding substance with said at least one of the cell membrane receptor binding factor and the membrane fusing substance, where present, being via a covalent bond or non-covalent interaction, and said complex being encapsulated in an envelope or capsid of viral origin.

14. The nucleic acid complex for nuclear import as claimed in claim 13, wherein the complex is encapsulated in a Sendai virus envelope.

15. An in vitro method of delivering a gene into cells comprising contacting a nucleic acid complex as claimed in claim 1 with the cells in vitro, wherein the nucleic acid is introduced into the cells and the gene is expressed.

16. The nucleic acid complex for nuclear transport as claimed in claim 8, wherein the binding of the polycationic binding substance with said importin protein and the at least one of the cell membrane receptor binding factor and the membrane fusing substance is via a biotin-avidin interaction in which said polycationic binding substance, said importin protein, and said at least one of the cell membrane receptor binding factor and the membrane fusing substance are biotinylated to form a complex via streptavidin interaction.

* * * * *

SEQUENCE LISTING

```
<160> NUMBER OF SEQ ID NOS: 1

<210> SEQ ID NO 1
<211> LENGTH: 7986
<212> TYPE: DNA
<213> ORGANISM: Artificial
<220> FEATURE:
<223> OTHER INFORMATION: Sequence of Biotin-Tag-Importin fusion protein
      expression vector

<400> SEQUENCE: 1
acgttatcga ctgcacggtg caccaatgct tctggcgtca ggcagccatc ggaagctgtg       60
gtatggctgt gcaggtcgta aatcactgca taattcgtgt cgctcaaggc gcactcccgt      120
tctggataat gttttttgcg ccgacatcat aacggttctg gcaaatattc tgaaatgagc      180
tgttgacaat taatcatcgg ctcgtataat gtgtggaatt gtgagcggat aacaatttca      240
cacaggaaac agtattcatg tcccctatac taggttattg gaaaattaag ggccttgtgc      300
aacccactcg acttcttttg gaatatcttg aagaaaaata tgaagagcat ttgtatgagc      360
gcgatgaagg tgataaatgg cgaaacaaaa gtttgaatt gggtttggag tttcccaatc      420
ttccttatta tattgatggt gatgttaaat taacacagtc tatggccatc atacgttata      480
```

```
tagctgacaa gcacaacatg ttgggtggtt gtccaaaaga gcgtgcagag atttcaatgc      540
ttgaaggagc ggttttggat attagatacg gtgtttcgag aattgcatat agtaaagact      600
ttgaaactct caaagttgat tttcttagca agctacctga aatgctgaaa atgttcgaag      660
atcgtttatg tcataaaaca tatttaaatg gtgatcatgt aacccatcct gacttcatgt      720
tgtatgacgc tcttgatgtt gttttataca tggacccaat gtgcctggat gcgttcccaa      780
aattagtttg ttttaaaaaa cgtattgaag ctatcccaca aattgataag tacttgaaat      840
ccagcaagta tatagcatgg cctttgcagg gctggcaagc cacgtttggt ggtggcgacc      900
atcctccaaa atcggatctg gttccgcgtg atccatgaaa actgaaggta acagtcaacg      960
gcactgcgta tgacgttgac gttgacgtcg acaagtcaca cgaaaacccg atgggcacca     1020
tcctgttcgg cggcggcacc ggcggcgcgc cggcaccggc agcaggtggc gcaggcgccg     1080
gtaaggccgg agagggcgag attcccgctc cgctggccgg caccgtctcc aagatcctcg     1140
tgaaggaggg tgacacggtc aaggctggtc agaccgtgct cgttctcgag gccatgaaga     1200
tggagaccga gatcaacgct cccaccgacg gcaaggtcga aaggtcctg gtcaaggagc     1260 gtgacgcggt gcagggcggt cagggtctca tcaagatcgg ggatctcgag ctcatcgaag     1320
gtcgcgaaaa gcttcagctg ggatccatgg agctcataac catcctcgag aagaccgtgt     1380
ctccggatcg gctggagctg gaagcggcgc agaagttcct cgagcgtgcg gccgtggaga     1440
atctgcccac gttccttgtg gaactgtcca gagtgctggc aaacccagga aacagtcagg     1500
ttgccagagt tgcagctggt ctacaaatta agaactcttt gacatcgaaa gatccagata     1560
tcaaggcaca ataccagcag aggtggctcg ctattgatgc taatgctcga cgggaagtca     1620
agaactatgt tttgcagacg ttgggcacag aaacgtaccg gcctagttcg gcctcacagt     1680
gtgtggctgg tattgcttgt gcagagatcc cagtaagcca gtggccagag ctaattcctc     1740
agctggtagc caatgtcaca aaccccaaca gcacagagca tatgaaagag tccacattgg     1800
aagctattgg ttacatttgc caagatatag acccagagca gctacaggat aagtccaatg     1860
agatcctgac tgccataatc caggggatga ggaaggagga gcctagtaac aatgtgaagc     1920
tggctgctac caatgcactc ctgaactcac tagagttcac caaagcaaac tttgacaaag     1980
agtctgaaag gcactttatc atgcaagtgg tctgtgaagc cacacagtgt ccagacacaa     2040
gggtaagagt ggctgctttta cagaatctag tgaagataat gtccttgtat taccagtaca     2100
tggagacata catgggtcct gccctttttg caatcacaat tgaagcaatg aaaagtgaca     2160
ttgatgaggt ggctctccaa gggatagagt tctggtccaa tgtctgtgat gaggaaatgg     2220
atttggccat tgaggcttca gaggcagcag agcaaggacg ccccccggag cacaccagca     2280
aattttacgc caagggagca ctgcagtact tggtgcccat cctcacacag acactgacta     2340
aacaggatga aaacgatgac gacgatgact ggaaccttg caaagcagct ggggtgtgcc     2400
tcatgctcct gtccacctgc tgtgaagatg acattgtgcc gcatgtcctt cccttttatta     2460 aagagcacat caagaacct gactggcgat accgggatgc agcagtgatg gcttttggca     2520
gtatcttgga aggaccagag cctaatcaac tgaaaccatt agtcatacag gctatgccca     2580
ccctaataga actaatgaaa gaccccagtg tagttgttcg agacacaaca gcgtggactg     2640
tgggcaggat ctgtgagctg ctgcctgaag ccgccatcaa cgatgtctac ctggcacccc     2700
ttttacagtg tctgattgag ggcctcagtg ctgagcccag ggtggcttca aatgtgtgct     2760 gggcttttc cagtctggct gaagctgcgt atgaagctgc agatgtagct gatgatcaag     2820
aagaaccagc cacctattgt ctgtcttctt cctttgaact tatagttcag aagctattgg     2880
```

```
agaccaccga cagacccgat ggacaccaga ataacctgag aagctctgcg tatgagtctc    2940
tcatggaaat cgtaaagaac agtgccaagg attgttaccc tgccgtgcag aagaccaccc    3000
tggtcattat ggaacggctg cagcaggtgc ttcagatgga gtcccatatc cagagcacat    3060
ccgacagaat ccagttcaat gacctccagt ctctactctg cgcgactctt cagaatgttc    3120
tccggaaagt gcagcatcaa gatgctctgc agatctctga tgtggtcatg gcctccctgt    3180
taaggatgtt ccaaagcaca gctgggtctg ggggagtgca agaagatgcc ctgatggcag    3240
ttagcacact ggtggaagtg ttgggtggtg aattcctcaa gtacatggag gcctttaaac    3300
cattcctggg cattggactg aaaaattatg ctgagtacca ggtatgtttg gcagctgttg    3360
gcttagttgg agacttgtgc cgagccctgc agtctaacat cttgcctttc tgtgacgagg    3420
tgatgcagct gctcctggag aacttgggga tgagaatgt ccacaggtct gtgaagccac    3480
agattctgtc tgtgtttggt gatattgctc ttgccattgg tggagagttt aaaaaatact    3540
tagaggttgt attgaatact ctacagcagg cctcccaagc ccaggttgac aagtcagact    3600
ttgacatggt ggattatctg aatgagctaa gagaaagctg cttggaagct tatacgggaa    3660
tcgtccaggg attgaaggga gatcaggaaa acgtacaccc ggatgtaatg ctggtacagc    3720
ccagagtaga atttattttg tcttttattg atcacattgc tggagatgag gatcatacgg    3780
acggagtggt agcctgtgct gctggtctga taggggactt gtgtacagcc ttcgggaagg    3840
atgtactgaa gttagtagaa gctaggccaa tgatccatga actattaact gaagggcgga    3900
gatcgaagac taacaaagca aagaccctcg ctacgtgggc aaccaaggaa ctgaggaaac    3960
tgaagaacca ggcttgaggt accatcgtga ctgactgacg atctgcctcg cgcgtttcgg    4020
tgatgacggt gaaaacctct gacacatgca gctcccggag acggtcacag cttgtctgta    4080
agcggatgcc gggagcagac aagcccgtca gggcgcgtca gcgggtgttg gcgggtgtcg    4140
gggcgcagcc atgacccagt cacgtagcga tagcggagtg tataattctt gaagacgaaa    4200
gggcctcgtg atacgcctat ttttataggt taatgtcatg ataataatgg tttcttagac    4260
gtcaggtggc acttttcggg gaaatgtgcg cggaaccccct atttgtttat ttttctaaat    4320
acattcaaat atgtatccgc tcatgagaca ataaccctga taaatgcttc aataatattg    4380
aaaaaggaag agtatgagta ttcaacattt ccgtgtcgcc cttattccct ttttgcggc    4440 attttgcctt cctgtttttg ctcacccaga aacgctggtg aaagtaaaag atgctgaaga    4500
tcagttgggt gcacgagtgg gttacatcga actggatctc aacagcggta agatccttga    4560
gagttttcgc cccgaagaac gttttccaat gatgagcact tttaaagttc tgctatgtgg    4620
cgcggtatta tcccgtgttg acgccgggca agagcaactc ggtcgccgca tacactattc    4680
tcagaatgac ttggttgagt actcaccagt cacagaaaag catcttacgg atggcatgac    4740
agtaagagaa ttatgcagtg ctgccataac catgagtgat aacactgcgg ccaacttact    4800
tctgacaacg atcggaggac cgaaggagct aaccgctttt ttgcacaaca tgggggatca    4860
tgtaactcgc cttgatcgtt gggaaccgga gctgaatgaa gccataccaa acgacgagcg    4920
tgacaccacg atgcctgcag caatggcaac aacgttgcgc aaactattaa ctggcgaact    4980
acttactcta gcttcccggc aacaattaat agactggatg gaggcggata agttgcagg    5040 accacttctg cgctcggccc ttccggctgg ctggtttatt gctgataaat ctggagccgg    5100
tgagcgtggg tctcgcggta tcattgcagc actggggcca gatggtaagc cctcccgtat    5160
cgtagttatc tacacgacgg ggagtcaggc aactatggat gaacgaaata gacagatcgc    5220
```

```
tgagataggt gcctcactga ttaagcattg gtaactgtca gaccaagttt actcatatat    5280
actttagatt gatttaaaac ttcattttta atttaaaagg atctaggtga agatcctttt    5340
tgataatctc atgaccaaaa tcccttaacg tgagttttcg ttccactgag cgtcagaccc    5400
cgtagaaaag atcaaaggat cttcttgaga tcctttttt ctgcgcgtaa tctgctgctt    5460
gcaaacaaaa aaaccaccgc taccagcggt ggtttgtttg ccggatcaag agctaccaac    5520 tcttttccg aaggtaactg gcttcagcag agcgcagata ccaaatactg tccttctagt    5580
gtagccgtag ttaggccacc acttcaagaa ctctgtagca ccgcctacat acctcgctct    5640
gctaatcctg ttaccagtgg ctgctgccag tggcgataag tcgtgtctta ccgggttgga    5700
ctcaagacga tagttaccgg ataaggcgca gcggtcgggc tgaacggggg gttcgtgcac    5760
acagcccagc ttggagcgaa cgacctacac cgaactgaga tacctacagc gtgagctatg    5820
agaaagcgcc acgcttcccg aagggagaaa ggcggacagg tatccggtaa gcggcagggt    5880
cggaacagga gagcgcacga gggagcttcc agggggaaac gcctggtatc tttatagtcc    5940
tgtcgggttt cgccacctct gacttgagcg tcgatttttg tgatgctcgt caggggggcg    6000
gagcctatgg aaaaacgcca gcaacgcggc ctttttacgg ttcctggcct tttgctggcc    6060
ttttgctcac atgttctttc ctgcgttatc ccctgattct gtggataacc gtattaccgc    6120
ctttgagtga gctgataccg ctcgccgcag ccgaacgacc gagcgcagcg agtcagtgag    6180
cgaggaagcg gaagagcgcc tgatgcggta ttttctcctt acgcatctgt gcggtatttc    6240
acaccgcata aattccgaca ccatcgaatg gtgcaaaacc tttcgcggta tggcatgata    6300
gcgcccggaa gagagtcaat tcagggtggt gaatgtgaaa ccagtaacgt tatacgatgt    6360
cgcagagtat gccggtgtct cttatcagac cgtttcccgc gtggtgaacc aggccagcca    6420
cgtttctgcg aaaacgcggg aaaaagtgga agcggcgatg gcggagctga attacattcc    6480
caaccgcgtg gcacaacaac tggcgggcaa acagtcgttg ctgattggcg ttgccacctc    6540
cagtctggcc ctgcacgcgc cgtcgcaaat tgtcgcggcg attaaatctc gcgccgatca    6600
actgggtgcc agcgtggtgg tgtcgatggt agaacgaagc ggcgtcgaag cctgtaaagc    6660
ggcggtgcac aatcttctcg cgcaacgcgt cagtgggctg atcattaact atccgctgga    6720
tgaccaggat gccattgctg tggaagctgc ctgcactaat gttccggcgt tatttcttga    6780
tgtctctgac cagacaccca tcaacagtat tattttctcc catgaagacg gtacgcgact    6840
gggcgtggag catctggtcg cattgggtca ccagcaaatc gcgctgttag cgggcccatt    6900
aagttctgtc tcggcgcgtc tgcgtctggc tggctggcat aaatatctca ctcgcaatca    6960
aattcagccg atagcggaac gggaaggcga ctggagtgcc atgtccggtt ttcaacaaac    7020
catgcaaatg ctgaatgagg gcatcgttcc cactgcgatg ctggttgcca acgatcagat    7080
ggcgctgggc gcaatgcgcg ccattaccga gtccgggctg cgcgttggtg cggatatctc    7140
ggtagtggga tacgacgata ccgaagacag ctcatgttat atcccgccgt taaccaccat    7200
caaacaggat tttcgcctgc tggggcaaac cagcgtggac cgcttgctgc aactctctca    7260
gggccaggcg gtgaagggca atcagctgtt gcccgtctca ctggtgaaaa gaaaaaccac    7320
cctggcgccc aatacgcaaa ccgcctctcc ccgcgcgttg gccgattcat taatgcagct    7380
ggcacgacag gtttcccgac tggaaagcgg gcagtgagcg caacgcaatt aatgtgagtt    7440
agctcactca ttaggcaccc caggctttac actttatgct tccggctcgt atgttgtgtg    7500
gaattgtgag cggataacaa tttcacacag gaaacagcta tgaccatgat tacgaattca    7560
ctggccgtcg ttttacaacg tcgtgactgg gaaaaccctg gcgttaccca acttaatcgc    7620
```

```
cttgcagcac atcccctttt cgccagctgg cgtaatagcg aagaggcccg caccgatcgc    7680
ccttcccaac agttgcgcag cctgaatggc gaatggcgct ttgcctggtt tccggcacca    7740
gaagcggtgc cggaaagctg gctggagtgc gatcttcctg aggccgatac tgtcgtcgtc    7800
ccctcaaact ggcagatgca cggttacgat gcgcccatct acaccaacgt aacctatccc    7860
attacggtca atccgccgtt tgttcccacg gagaatccga cgggttgtta ctcgctcaca    7920
tttaatgttg atgaaagctg gctacaggaa ggccagacgc gaattatttt tgatggcgtt    7980
ggaatt                                                               7986
```